United States Patent [19]

Schumann

[11] Patent Number: Plant 5,939

[45] Date of Patent: Apr. 14, 1987

[54] GERANIUM PLANT NAMED BOLERO

[75] Inventor: Ingeborg Schumann, Bad Ems, Fed. Rep. of Germany

[73] Assignee: Fischer Geraniums, Inc., Netherlands Antilles

[21] Appl. No.: 761,098

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Bolero having red flower color; semi-double flower form; dark green foliage; very good chlorophyll quality for transportation; slight zonation; good weather resistance; early flowering response; and compact growth habit.

1 Drawing Figure

The present invention comprises a new and distinct cultivar of geranium, botanically known as *Pelargonium zonale,* and hereinafter referred to by the cultivar name Bolero.

Bolero is a product of a planned breeding program which had the objective of creating new geranium cultivars having dark green foliage, red flower color, semi-double flower form, good chlorophyll quality for shipping, compact growth habit and very fast rooting.

Bolero was originated from a hybridization made by Ingeborg Schumann in a controlled breeding program in Hillscheid, Federal Republic of Germany in 1981. The female parent was an inbred line of Vesuv. The male parent of Bolero was Bern of the "Pelfi" ® series of Pelargonien-Fischer KG, Hillscheid, Federal Republic of Germany. Both parents are unpatented.

Bolero was discovered and selected as one flowering plant within the progeny of the stated cross by Ingeborg Schumann on June 5, 1982 in a controlled environment in Hillscheid, Federal Republic of Germany.

The first act of asexual reproduction of Bolero was accomplished when vegetative cuttings were taken from the initial selection in January of 1983 in a controlled environment in Hillscheid, Federal Republic of Germany by a technician working under formulations established and supervised by Ingeborg Schumann. Horticultural examination of selected units initiated in the spring of 1983 and 1984 has demonstrated that the combination of characteristics as herein disclosed for Bolero are firmly fixed and are retained through successive generations of asexual reproduction.

Bolero has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Bolero, which in combination distinguish this geranium as a new and distinct cultivar.

1. Red flower color.
2. Semi-double flower form.
3. Very dark green foliage.
4. Very good chlorophyll quality for transportation.
5. Early flowering response and floriferous habit.

6. Good weather resistance.
7. Very little zonation.
8. Compact and vigorous growth habit.

The accompanying photographic drawing shows typical flower and foliage characteristics of Bolero, with colors being as true as possible with illustrations of this type.

Bolero is similar in many respect to Tango, a cultivar of Applicant disclosed in a pending applcation. The foliage and flower color are similar, but Bolero has smaller and more numerous umbels and a more vigorous growth habit than Tango.

In the following description color references are made to The Royal Horticultural Society Colour Chart. The color values were determined between 10:00 a.m. and 11:00 a.m. on May 22, 1985 under 35,000 Lux light intensity at Hillscheid, Federal Republic of Germany.

Classification:

*Botanical.*—A hybrid of the genus Pelargonium l'hert and species *Pelargonium zonale.*

*Commercial.*—Bolero.

INFLORESCENCE

A. Umbel:

*Average diameter.*—100 mm.

*Average depth.*—55 mm.

*Peduncle length.*—190 mm.

*Pedicel length.*—30 mm.

B. Corolla:

*Average diameter.*—50 mm.

*Form.*—Semi-double; asymmetric.

*Color (general tonality from a distance of three meters).*—Red. Upper surface: 44A.

C. Bud:

*Shape.*—Round to oval.

*Color.*—Red.

D. Reproductive organs:

*Androecium.*—Some sterile; some 6 to 8 stamens.

*Gynoecium.*—4–5 lobed stigma.

E. Spring flowering response period: In Hillscheid, Federal Republic of Germany, in 1983, 55% of plants opened with at least one flower 13 weeks after planting of unrooted cuttings.

F. Outdoor flower production: The total flower count in 1983 in Hillscheid, Federal Republic of Germany, was between 42 and 45 flowers per plant for the June through October observation period.

G. Durability: Very good.

PLANT

A. Foliage:

*Form.*—Kidney shaped.

*Margin.*—Wavy, crenated.

*Color.*—Top surface: Dark green. Zonation: Weak zonation.

*Tolerance of botrytis.*—Good.

B. General appearance and form:

*Internode length.*—22 mm.

*Branching pattern.*—3.5 branches per plant.

*Height.*—210 mm.

I claim:

1. A new and distinct cultivar of geranium named Bolero, as described and illustrated, and particularly characterized by its red flower color; semi-double flower form; dark green foliage; very good chlorophyll quality for transportation; slight zonation; good weather resistance; early flowering response; and compact growth habit.

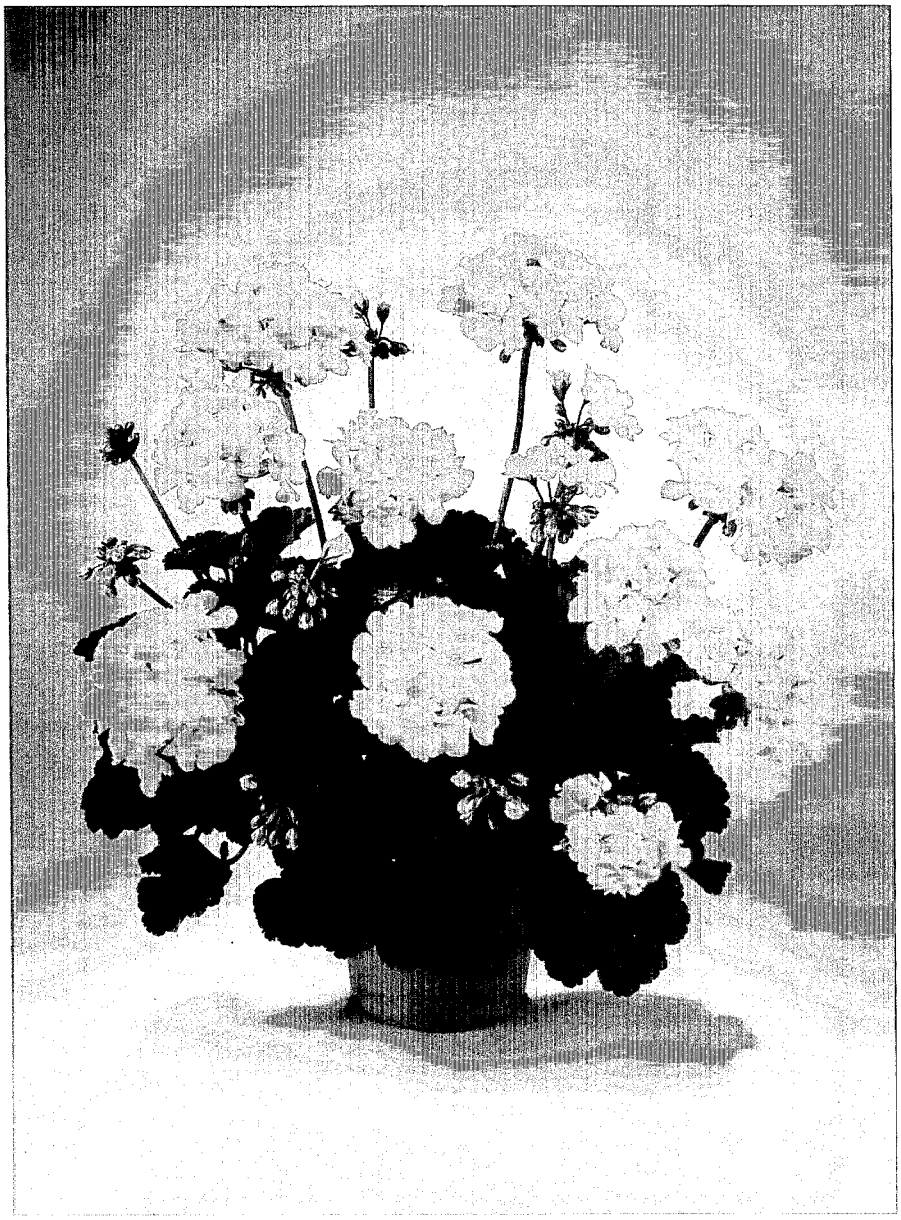

* * * * *